United States Patent [19]

Keblys

[11] 3,935,228

[45] Jan. 27, 1976

[54] PREPARATION OF COBALT COMPLEX

[75] Inventor: Kestutis A. Keblys, Southfield, Mich.

[73] Assignee: Ethyl Corporation, Richmond, Va.

[22] Filed: Oct. 23, 1973

[21] Appl. No.: 408,635

Related U.S. Application Data

[63] Continuation of Ser. No. 141,993, May 10, 1971, abandoned.

[52] U.S. Cl.... 260/270 J; 260/410.9 R; 260/439 R; 260/497 C; 260/497 R; 260/604 HF
[51] Int. Cl.$^2$.............. C07D 213/16; C07D 215/06
[58] Field of Search ......... 260/270 J, 497 R, 497 C, 260/604 HF, 439 R, 410.9 R; 423/417, 418

[56] References Cited

UNITED STATES PATENTS 3,725,534    4/1973    Reisch .......................... 260/604 HF

FOREIGN PATENTS OR APPLICATIONS 1,199,550    7/1970    United Kingdom .......... 260/604 HF Primary Examiner—Donald G. Daus
Assistant Examiner—Mark L. Berch
Attorney, Agent, or Firm—Donald L. Johnson; Robert A. Linn

[57] ABSTRACT

A process for preparing cobalt complexes and their use as hydroesterification catalysts are disclosed.

26 Claims, No Drawings

PREPARATION OF COBALT COMPLEX

CROSS REFERENCE TO RELATED APPLICATION

This application is a continuation of copending application Ser. No. 141,993, filed May 10, 1971, now abandoned.

BACKGROUND OF THE INVENTION

The present invention is directed to preparation of cobalt containing complexes and their use to improve hydroesterification reactions.

Hydroesterification involves the reaction of an olefinic compound, CO and an alcohol in the presence of a suitable catalyst, to produce ester generally at elevated temperatures and pressures. Cobalt carbonyl and cobalt compounds, such as organic and inorganic salts of cobalt, are most commonly used catalysts. Representative hydroesterification processes are disclosed in U.S. Pat. Nos. 2,542,767; 2,689,261; and 2,768,968. Use of pyridine promoters and/or hydrogen to improve the rate of such cobalt catalyzed hydroesterification reactions is also known; see U.S. Pat. No. 3,507,891; A. Matsuda and H. Uchida, *Bull. Chem. Soc. Japan*, 38, 710, (1965); V. Gankin, N. Gordina, M. Katsnelson, D. Rudkovskii, *Zh. Pr. K.*, 40, 1862, (1967).

When cobalt carbonyl is used as the catalyst component, no induction period is required for the hydroesterification reaction to begin after the reactants and catalyst component have been charged and the reaction temperature is reached. Cobalt carbonyl, however, is expensive and requires special handling procedures. When other less expensive cobalt compounds, such as cobalt salts, are used as catalyst components, an induction period is required before the hydroesterification reaction begins. This induction period can be substantial, especially where high molecular weight olefinic reactants are used. Addition of hydrogen to cobalt salt catalyzed hydroesterification is known to reduce the induction period; however, the addition of hydrogen results in the formation of undesirable aldehyde-type by-products.

It has been discovered that cobalt complexes can be prepared by reacting cobalt compounds with carbon monoxide, hydrogen, a pyridine, and an alkanol; and that these complexes can be used to catalyze the hydroesterification reaction without requiring any induction period and without causing undesirable by-product aldehyde formation.

SUMMARY OF THE INVENTION

A process for preparing cobalt complexes which comprises reacting a suitable cobalt salt, carbon monoxide, hydrogen and a pyridine in the presence of an alkanol. The complex catalyzes hydroesterification without requiring an induction period and without causing production of undesirable aldehyde-type by-products.

DESCRIPTION OF THE PREFERRED EMBODIMENTS

An embodiment of this invention is a process for preparing cobalt complexes which comprises reacting (1) cobalt compound, (2) carbon monoxide, (3) hydrogen, (4) a pyridine, and (5) $C_1$-$C_{10}$ alkanol. Preferred processes use cobalt salts $C_2$-$C_{20}$ carboxylic acids, or cobalt salts of inorganic acids. Pyridine is used in more preferred processes; and methanol is the alkanol used in a most preferred process.

A wide variety of cobalt compounds can be used in the above process. This includes binary inorganic cobalt compounds, cobalt salts of inorganic acids as well as cobalt salts of organic acids. Illustrative examples of useful inorganic cobalt compounds are cobalt oxides, sulfides, cyanides, cobalt salts of inorganic acids such as $H_2SO_4$, $H_2SO_3$, $HNO_3$, halogen acids, the phosphorous acids, the boric acids, carbonic acids and the like. Cobalt carbonate is an especially useful inorganic cobalt compound.

Useful organic cobalt compounds include cobalt salts of sulfonic acids, phosphorous containing acids, carboxylic acids, especially the $C_2$-$C_{20}$ carboxylic acids and the like. Illustrative examples of such cobalt compounds are cobalt acetate, cobalt naphthenate, cobalt eicosanoate, cobalt 2ethylhexanoate, cobalt oxalate, cobalt benzenesulfonate, cobalt methylphosphonate, and the like.

Pyridines which are useful in the above process include pyridine itself as well as substituted pyridines. These substituted pyridines may have one or more substituents selected from hydrocarbyl, halogen, hydroxy, carbonyl, cyano, and the like. Illustrative examples of such substituted pyridines are 2-hydroxypyridine, 3-iodopyridine, 4-cyanopyridine, 4-acetylpyridine, 4(diphenyldimethyl)pyridine, 4,4'-trimethylenepyridine, isoquinoline, 2-ethyl-4-chloropyridine, 2,6dimethyl-4-phenylpyridine and the like. The $C_1$-$C_8$ alkyl substituted pyridines are more preferred. Examples of these preferred pyridines are 2-methylpyridine, 3,5-dimethylpyridine, 4-ethyl-3,3-dimethylpyridine, 4-butylpyridine, 3,4-diethylpyridine, 2-cyclohexylpyridine, 3-tert-butylpyridine, and the like. The alkyl substituted pyridines which have no substituent in the position ortho to the nitrogen atom in the pyridine ring are more preferred. Pyridine is most preferred.

The process requires an alkanol. Especially useful alkanols are $C_1$-$C_{10}$ alkanols. Examples of such alkanols are ethanol, methanol, n-decanol, 2-ethylhexanol, tert-butanol, 2-heptanol, cyclohexanol, and the like. The $C_1$-$C_4$ monohydroxy alkanols are more preferred. Methanol is a most preferred alkanol.

Hydrogen and carbon monoxide are also required reactants. The molar ratio of $H_2$:CO used can be varied. Molar ratios of 1:10 to 10:1 can be used; ratios of 1.5:1 to 1:3 are preferred; more preferred molar ratios are 1:1 to 1:3.

The process for preparing the complex is carried out under pressure. The pressure is for the most part that exerted by the CO and $H_2$ reactants. Reaction pressures ranging from 1,000 to 10,000 p.s.i.g. can be used. Pressures ranging from 1,500 to 3,000 p.s.i.g. are preferred. Preparation of the complex is carried out at elevated temperatures ranging from about 100° to about 250°. Preferred reaction temperatures are from 130° to 180°.

The amount of the pyridine used can be varied. Ordinarily, two or more moles of pyridine per atom of cobalt is provided in the process. The amount of alkanol used is also varied. Ordinarily, the amount of alkanol is based on the amount of the pyridine. Volume ratios of alkanol:pyridine ranging from 3:1 to 1:3 can be used. Alkanol:pyridine volume ratio of about 1:1 is more preferred.

This invention also embodies the use of the novel cobalt complexes as hydroesterification catalysts. Hydroesterification comprises the reaction of an olefinic compound with an alcohol and CO at elevated temperatures and pressures.

This reaction is illustrated by the following equation:

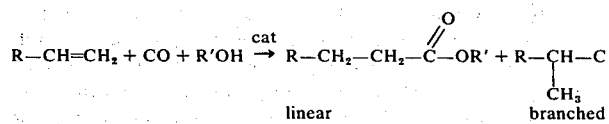

linear / branched

The ester products obtained are mixtures of branched and linear esters. The hydroesterification is ordinarily carried out at elevated temperatures (75°C.–200°C.) and under pressure, primarily due to CO, ranging from about 500 to about 5,000 p.s.i.g. Olefins which are used in the hydroesterification process are unsaturated organic compounds having at least one non-aromatic carbon to carbon double bond, and having from 2 to about 40 carbon atoms. They include compounds having other functional groups such as carboxy, carbonyl, halide, aryl groups and the like, provided that these functional groups do not adversely affect the hydroesterification reaction of the present extraction process. Branched as well as straight chain, cyclic and alicyclic are included. Useful olefins are ethyl acrylate, oleic acid, 2-chlorododecene-1, 6-phenylundecene-1, ricinoleic acid, 3-hydroxyheptadecene, and the like.

More preferred olefins are hydrocarbon monoolefins including the alpha as well as internal olefins. Examples of useful hydrocarbon monoolefins are ethylene, butene-1, pentene-2, cyclooctene, eicosene-1, hexadecene-2, octacosene-4, 4-butyldecene-1, tetracontene-1, 5,7,11-trimethyldodecene-1, and the like. Mixtures of alpha and internal olefins are also useful. In addition, commercial mixtures of olefins obtained for example from Ziegler catalyzed low molecular weight olefins such as ethylene or propylene and those obtained by dehydrogenation of suitable paraffins and the like are also useful. These commercial mixtures are generally mixtures of various homologous olefins such as $C_4$, $C_6$, $C_8$ olefins; $C_{12}$, $C_{13}$, $C_{14}$, $C_{15}$, $C_{16}$ olefins; $C_8$, $C_{10}$, $C_{12}$, $C_{14}$, $C_{16}$ olefins; $C_{30}$–$C_{36}$ olefins; $C_{22}$, $C_{24}$, $C_{26}$ olefins and the like.

The alkanol reactants in the hydroesterification process are normally liquid alkanols having up to 12 carbon atoms. They include primary, secondary, and tertiary alkanols. They are exemplified by 2-dodecanol, tert-butanol, 2-ethylhexanol, cyclohexanol, 2,2-dimethylpropanol and the like. Monohydroxy alkanols having from 1-5 carbon atoms are more preferred. Examples of such alkanols are ethanol n-pentanol, 2-methylpropanol and isopropanol, sec-butanol and the like. The primary monohydroxy $C_1$–$C_5$ alkanols are more preferred. Methanol is a most preferred alkanol.

Although not required in the hydroesterification reaction, use of a pyridine promoter is preferred. Suitable pyridine promoters include pyridine and substituted pyridines such as the halopyridines, alkylpyridines, quinolines, cyanopyridines, acylpyridines, nitropyridines, and the like. Preferred pyridines are those which have no substituent in the alpha position. They are exemplified by $C_1$–$C_6$ alkylpyridines (β-picoline, 4-ethyl-3,5-dimethylpyridine, 4,4'-trimethylenedipyridine, 3-hexylpyridine, 3,5-dimethylpyridine, 3,5-diethylpyridine, 4-cyclohexylpyridine); acylpyridines (3-butyrylpyridine, 4-propionylpyridine, 4-acetyl-3-methylpyridine), and the like. Other useful pyridine promoters are described in U.S. Pat. No. 3,507,891, issued Apr. 21, 1970. Pyridine is a most preferred promoter.

When used, the amount of pyridine promoter can be varied over a wide range. A practical upper limit is about 250 moles of pyridine promoter per mole of cobalt in the catalyst although greater amounts can be used. A preferred range is 6–50 moles of pyridine promoter per mole of cobalt.

The pyridine promoter effects improvement in the reaction rate and/or the ratio of linear to branched ester product obtained in the hydroesterification reaction. An improved hydroesterification process featuring the use of a pyridine promoter is set forth below.

GENERAL HYDROESTERIFICATION PROCEDURE

The olefin, catalyst, alcohol and promoter (where added) were charged to a suitably sized autoclave. The autoclave was then sealed and flushed twice with carbon monoxide (CO) and then brought to the desired reaction pressure. Where hydrogen was also added to the autoclave, the CO was charged first, followed by the $H_2$. Then, the autoclave was heated to the desired reaction temperature in a heated shaker. The reaction was continued at this temperature in the shaker for the desired length of time. The autoclave was then cooled to room temperature with compressed air and vented. The yield of product ester was then obtained; and it was analyzed via gas liquid chromatography(glc).

Table 1 contains data from first series of examples which illustrates the promoter effect of pyridines on octene-1 hydroesterification. The following reactants and reaction parameters were used for Examples 1–8.

| Examples 1–8 | | |
|---|---|---|
| | Compound | Quantity |
| Olefin | octene-1 | 0.4 moles |
| Catalyst | $Co_2(CO)_8$ | 3 grams |
| Alcohol | methanol | 79 grams |

Reaction time was 3 hours, reaction temperature was 175°C, CO pressure at 25°C. was 200 atmosphere.

Table 1

| | | | Promoter Effect Of Pyridines | | | | | | |
|---|---|---|---|---|---|---|---|---|---|
| | | | | Product Composition | | Ester % Isomers | | | |
| Example[1] | Promoter | Moles | Product Yield | Acetal + Aldehyde | $C_8$ Methyl Esters | −1 | −2 | −3 | −4 |
| 1 | None | | 39% | 15% | 85% | 58 | 21 | 11 | 10 |
| 2 | Pyridine | 0.3 | 90% | 3% | 97% | 78 | 14 | 4.5 | 3.5 |

Table 1-continued

Promoter Effect Of Pyridines

| Example[1] | Promoter | Moles | Product Yield | Product Composition Acetal + Aldehyde | $C_8$ Methyl Esters | Ester % Isomers -1 | -2 | -3 | -4 |
|---|---|---|---|---|---|---|---|---|---|
| 3 | β-Picoline | 0.3 | 81% | 1% | 99% | 81 | 13 | 3.5 | 3.5 |
| 4 | γ-Picoline | 0.3 | 77% | 1% | 99% | 81 | 14 | 3 | 2 |
| 5 | 4-Acetyl-pyridine | 0.3 | 64% | — | 100% | 74 | 16 | 5.5 | 4.5 |
| 6 | α-Picoline | 0.3 | 58% | 10% | 90% | 56 | 22 | 12 | 10 |
| 7 | 2,6-Dimethyl pyridine | 0.3 | 46% | 9% | 91% | 58 | 21 | 12 | 9 |
| 8 | Quinoline | 0.24 | 74% | — | 100% | 54 | 23 | 14 | 9 |

[1]The carbon monoxide used in Example 1 also contained 4% $H_2$; in Examples 2–8, the CO contained 3–5% $H_2$.

Analogous results are obtained using the general procedure of Examples 2–5 when $C_7$ ethyl esters are prepared from hexene and ethanol; $C_{31}$ methyl esters are prepared from triacontene and methanol; $C_{21}$ ethyl esters are prepared from eicosene and ethanol; $C_{18}$ isopropyl esters are prepared from heptadecene and isopropanol; $C_{13}$ pentyl esters are prepared from triisobutylene and pentanol; $C_{13}$ butyl esters are prepared from cyclododecene and butanol; mixtures of methyl esters are prepared from a commercial olefin mixture comprising even numbered, predominately α-monoolefins in the $C_{12}$-$C_{32}$ carbon chain range, and the like.

Sufficient cobalt complex is used to provide from about 0.005 to 0.10 moles of cobalt per mole of olefinic reactant.

An advantage of using the present cobalt complex as the hydroesterification catalyst is that is it permits the use of a relatively inexpensive cobalt compound without addition of hydrogen to the system to provide a catalyst which requires essentially no induction or activation period. This is especially advantageous where a catalyst is fed to a continuous hydroesterification system such as might be utilized in a commercial consideration. In such an operation any induction period which might be required after charging a catalyst, and particularly make-up catalyst, (that is, catalyst added to replace catalyst lost during the course of the process), would have an adverse effect on the efficiency of the operation. Thus, e.g. if the cobalt compound added as the catalyst required a 30-minute activation or induction period (1) this would then increase the reaction sequence by 30 minutes, and/or (2) might require an extra reaction vessel to hold the reactants and catalyst during this induction period. By first preparing the cobalt complex as described above, it is clear that the overall hydroesterification would be more economical and more efficient.

The following examples will illustrate the process for preparing the novel cobalt complexes and their use in hydroesterification reactions. The carbon monoxide used in all the examples was C. P. or commercial grade, which is substantially free from hydrogen.

EXAMPLE 1

A. Preparation of Cobalt Complex

An autoclave was charged with 4.1 grams (g) cobalt carbonate, 96 milliliters (mls) methanol and 60 mls pyridine. The autoclave was sealed and pressured with 500 p.s.i.g. of hydrogen and 1,000 p.s.i.g. of carbon monoxide. The mixture was then heated at 150°C. for 3.5 hours with stirring. Total pressure drop during this period was 350 p.s.i.g.

The autoclave was then cooled and vented. The reaction mixture was filtered. The filtrate was red-orange in color and contained soluble cobalt complex. On analysis, this filtrate was shown to contain 9.0 milligrams (mg) cobalt/ml. which indicated 69% conversion of cobalt carbonate to the cobalt complex.

B. Hydroesterification Using the Above Cobalt Complex

An autoclave was charged with 80 g of 1-dodecene (91% α-isomer and 4% vinylidene isomer) and 62 mls of the red-orange cobalt complex solution prepared in A.) above. The red-orange filtrate already contained sufficient methanol and pyridine promoter so that no further addition of either of these components was required for the hydroesterification. The autoclave was then sealed and pressured to 1,600 p.s.i.g. with CO and heated with stirring for 1 hour at 150°C. Analysis of the product of this hydroesterification showed that 69% of the 1-dodecene charge was converted to methyl tridecanoates, 82.6% of which were the linear methyl tridecanoate isomer.

Analogous cobalt complex is prepared when using a substituted pyridine such as 3-methylpyridine, 3,5-diethylpyridine, 2-cyanopyridine, or 4-hexylpyridine in place of pyridine in the Example 1A. preparation.

EXAMPLE 2

A. Preparation of Cobalt Complex

An autoclave was charged with 46.1 g cobalt carbonate, 140 mls pyridine and 40 mls methanol. The autoclave was sealed and pressured to 1,620 p.s.i.g. with 2:1 carbon monoxide: hydrogen. This mixture was stirred for 22 hours at 150°C. During the course of the reaction period, the autoclave was repressured five times with carbon monoxide (to 3,100 p.s.i.g. each time) and twice with hydrogen (to 2,000–2,500 p.s.i.g.). The total pressure drop during this reaction period was 6,900 p.s.i.g. at 150°C.

At the end of this time, the autoclave was cooled and vented. The reaction mixture was filtered, yielding 199 mls of cobalt complex containing dark red filtrate. Analysis of the filtrate showed it to contain 1.36 millimoles (mmoles) cobalt/ml.

B. Hydroesterification Using the Cobalt Complex Prepared in 2A.

An autoclave was charged with 12 mls of cobalt containing filtrate from 2A. (this contained 16.3 mmoles cobalt, 2.4 mls methanol and 8.4 mls of pyridine), 78 mls 1-dodecene, 26.3 mls methanol and 8.3 mls pyridine. The autoclave was then flushed with CO, sealed and pressured to 1,980 p.s.i.g. with carbon monoxide.

The autoclave was then heated to 150°C. and stirred at this temperature for 1 hour. The pressure drop was 465 p.s.i.g.

At the end of this time, the autoclave was cooled and vented. Vapor Phase Chromatographic (VPC) analysis of this reaction mixture showed that 65.2% of the dodecene was converted to methyl tridecanoate esters, of which 84.3% were the linear methyl tridecanoate isomer.

At most, only traces of undesirable by-products, e.g. aldehydes, aldols, are present in the hydroesterification products of Examples 1 and 2.

Analogous cobalt complex is prepared when other alkanols such as ethanol, n-decanol, 2-methyl butanol, or isoamyl alcohol are used in place of methanol in Examples 1A. or 2A. Similar complexes are obtained when cobalt carbonate in Examples 1A. or 2A. is replaced with equivalent amounts of cobalt as cobalt naphthenate, cobalt bromide, cobalt orthophosphite, cobalt propionate, cobalt cyanide, cobalt oxalate, cobalt dodeconoate, or cobalt hexanoate. Pyridine: methanol volume ratios of 3:1, 1:3, 2.5:1 or 1:2.5 give comparable results in Examples 1A. or 2A.

The preparation of cobalt complexes of Examples 1A. and 2A., can also be carried out at 100°C., 250°C., 200°C., 130°C., 170°C., or 180°C.; reaction pressures of 1,000 p.s.i.g., 10,000 p.s.i.g., 5,000 p.s.i.g., 1,500 p.s.i.g., or 3,000 p.s.i.g. are also used with analogous effectiveness. Similar results are obtained in Examples 1A. and 2A. when molar ratios of $H_2:CO$ of 1:10, 1.5:1, 1:3, 10:1 or 5:1 are used.

EXAMPLE 3

An autoclave was charged with 17.5 g of cobalt carbonate, 35 ml pyridine, and 35 ml methanol. The autoclave was sealed and pressured to 1,800 p.s.i.g. with 2:1 carbon monoxide:hydrogen. The autoclave was heated to 150°C. and stirred at this temperature for 2.5 hours. The autoclave was repressured once with carbon monoxide to 2,300 p.s.i.g. after one hour and 45 minutes.

At the end of the 2.5 hours, the autoclave was cooled and vented. The reaction mixture was filtered, yielding 84 mls of dark red filtrate. Analysis showed the filtrate to contain 0.10 g cobalt/ml, corresponding to 99.5% yield of soluble cobalt complex based on cobalt carbonate charged. This cobalt complex effectively catalyzes hydroesterification without requiring an induction period.

Comparable cobalt solutions are prepared when cobalt compounds described herein are used in place of cobalt carbonate in processes such as those illustrated by the above examples. Thus, useful cobalt complexes can be prepared from compounds such as cobalt nitrate, cobalt chloride, cobalt oxide, cobalt sulfate, cobalt phosphate and other inorganic cobalt compounds; or cobalt acetate, cobalt sulfonate, cobalt oxalate, cobalt naphthenate, and other similar organic cobalt compounds.

Although the above examples illustrate effectiveness of the cobalt complexes as hydroesterification catalysts where a pyridine promoter is utilized and an alpha olefin is the reactant, the cobalt complexes of this invention are analogously effective in hydroesterification reactions where no pyridine promoter other than that in the complex is utilized and/or when other olefinic reactants are used. In addition, where a pyridine promoter is used in the hydroesterification, the cobalt complex need not be prepared using the same pyridine which is used as the hydroesterification promoter. Following is a table of representative hydroesterification reactant systems which are effectively catalyzed by cobalt complexes of the present invention:

| Monoolefin | Alcohol | Promoter | Product |
|---|---|---|---|
| Ethylene | n-propanol | none | → propyl $C_3$ esters |
| Mixture of $C_4$, $C_8$ | ethanol | 4-methyl-pyridine | → ethyl $C_5$, $C_7$ esters |
| Mixed (*) $C_{12}$, $C_{14}$, $C_{18}$ | methanol | 3,5-dibutyl-pyridine | → methyl $C_{13}$, $C_{15}$, $C_{17}$ esters |
| 2-Tetradecene | methanol | 3-butyl-pyridine | → methyl $C_{15}$ esters |
| Mixture of $C_{10}$, $C_{11}$, $C_{12}$ (60% $C_{17}$ α (40% $C_{17}$ internal | 2-butanol 1-pentanol | none isoquinoline | → butyl $C_{11}$, $C_{12}$, $C_{13}$ esters pentyl $C_{18}$ → esters |

(*)includes terminal olefins (α and vinylidene) and internal, with α over 40%.

As pointed out previously, one of the advantages of using the novel cobalt complexes of this invention as catalysts is that no induction period is required when such a complex is used as a catalyst. When, for example, the cobalt complex of Example 3 is used to catalyze the reaction of a $C_2$–$C_{40}$ olefin, a $C_1$–$C_5$ alkanol and CO, pressure up-take on reaching the reaction temperature is immediate, indicating that the reaction is proceeding with no induction period; but if the same hydroesterification reaction is carried out by utilizing an equal amount (*) of cobalt carbonate as the catalyst, on reaching reaction temperature, a substantial amount of time is required before any pressure drop is observed, indicating that this system requires a substantial induction period.

(*) Based on moles of cobalt

The following example illustrates that an alkanol is essential in order to prepare the cobalt complex of the present invention.

EXAMPLE 4

An autoclave was charged with 37.4 g cobalt carbonate and 150 mls pyridine. The autoclave was then sealed and pressured with 50 p.s.i.g. of hydrogen and 1,050 p.s.i.g. of carbon monoxide; it was stirred for 3 hours at 150°C. Substantially no gas up-take was observed during this entire period, indicating that no reaction was occurring.

The autoclave was cooled and vented; 30 mls of methanol was added thereto and the autoclave was sealed and repressured with 570 p.s.i.g. of hydrogen and 1,040 p.s.i.g. carbon monoxide. Gas up-take began as soon as the autoclave was heated to 150°C. The reaction was continued at this temperature for 18 hours, during which time the autoclave was repressured several times with carbon monoxide. Total gas up-take during the 18-hour period was 3,655 p.s.i.g.

The autoclave was then cooled and vented and the reaction mixture was filtered, yielding an orange-red cobalt containing filtrate. Analysis showed the filtrate to contain 0.963 mmoles of cobalt/ml.

Example 4 clearly shows that an alkanol is essential in order to prepare the present cobalt complex. When the preparation was attempted with cobalt carbonate, pyridine, $H_2$, CO and no alkanol, there was no evidence of reaction after 3 hours at 150°C. On adding methanol to the reaction mixture, reaction began immediately on heating the reactants to 150°C.

The effectiveness of the cobalt complex obtained in Example 4, as a hydroesterification catalyst, is demonstrated in the following example.

EXAMPLE 5 i. An autoclave was charged with 17.0 ml of Example 4 cobalt containing filtrate (this filtrate charge contained 163 mmoles of cobalt, 14.1 ml of pyridine and 2.7 ml methanol), 78.0 ml 1-dodecene, 26.0 ml methanol, and 2.6 ml pyridine. The autoclave was sealed and pressured to 2,100 p.s.i.g. with commercial CO (98%, containing less than 0.1% $H_2$). The mixture was then heated to 150°C., with stirring, and the reaction was continued at this temperature for 1 hour. Total pressure drop during this period was 625 p.s.i.g.

The autoclave was then cooled and vented. Analysis of the product by VPC showed 78.1% conversion of dodecene to methyl tridecanoate esters, 83.0% of which was the linear methyl tridecanoate ester.

ii. An autoclave was charged with 17 mls of the Example 4 cobalt complex containing filtrate (this filtrate charge contained 16.3 mmoles cobalt, 14.1 mls pyridine, 2.7 mls methanol), 78 mls 1-dodecene, 26 mls methanol and 2.6 mls pyridine. The autoclave was then sealed and pressured to 690 p.s.i.g. with CO and was heated with stirring to 150°C. The pressure at this temperature rose to 1,000 p.s.i.g. and was maintained between 950 and 1,050 p.s.i.g. by repressuring the autoclave with CO as needed during the reaction period. The reaction was continued for 1 hour at 150°C.

The autoclave was then cooled and vented. Analysis showed a 45.1% conversion of dodecene to methyl tridecanoate esters, 87.5% of which were the linear tridecanoate isomer.

iii. When the hydroesterification reaction of (ii) was carried out at a pressure maintained at about 800 p.s.i.g. at 150°C., it resulted in a 29.4% dodecene conversion to methyl tridecanoate esters, of which 87.5% were the linear methyl tridecanoate isomer.

The cobalt complexes of the present invention are shown to be useful as hydroesterification catalysts. In addition, these complexes also find use as catalysts in other carbonylation reactions such as hydroformylation, hydrocarboxylation and the like.

The ester products from the improved hydroesterification process described herein can be used as plasticizers and solvents; or they can be hydrolyzed to yield the corresponding acids which may find use as soap intermediates.

The present invention as described herein embodies novel cobalt complexes, a process for preparing the complexes and use of the complexes to catalyze hydroesterification.

Claims to the invention follow.

I claim:

1. A process for preparing solutions in pyridine/methanol of cobalt complexes which consists essentially of reacting (1) cobalt compound selected from cobalt oxides, cobalt sulfides, cobalt cyanides, cobalt salts of $H_2SO_4$, $H_2SO_3$, $HNO_3$, halogen acids, phosphorus acids, boric acids and carbonic acids, organic cobalt salts of sulfonic acids, phosphorus containing acids, and $C_2$–$C_{20}$ carboxylic acids, (2) carbon monoxide, (3) hydrogen, (4) a pyridine selected from pyridine and substituted pyridines wherein the substituents are selected from $C_1$–$C_6$ hydrocarbon alkyl, and (5) $C_1$–$C_{10}$ alkanol such that (i) the molar ratio of $H_2$:CO is from 1:10 to 10:1; (ii) the molar ratio of said pyridine:cobalt is greater than about 2:1, and (iii) the volume ratio of pyridine:alkanol is from 3:1 to 1:3, at pressures ranging from about 1,000 to about 10,000 p.s.i.g., and temperatures ranging from 100°C. to 250°C.

2. The process of claim 1, wherein said $H_2$:CO molar ratio is 1.5:1 to 1:3 and said pyridine:alkanol volume ratio is about 1:1.

3. The process of claim 1 wherein said pyridine is pyridine.

4. The process of claim 1 wherein said alkanol is methanol.

5. The process of claim 4 wherein said cobalt compound is a cobalt salt of a $C_2$–$C_{20}$ carboxylic acid and said pyridine is pyridine.

6. The process of claim 4 wherein said alkanol is methanol.

7. The process of claim 6 wherein said cobalt compound is cobalt carbonate.

8. The process of claim 7 wherein said $H_2$:CO ratio is 1:1 to 1:3.

9. The process of claim 8 wherein said pyridine methanol volume ratio is about 1:1.

10. The process of claim 9 wherein said $H_2$:CO ratio is about 1:2.

11. The cobalt complex prepared by the process of claim 1 wherein said cobalt compound is cobalt salt of a $C_2$–$C_{20}$ carboxylic acid, said alkanol is methanol and said pyridine is pyridine.

12. The cobalt complex prepared by the process of claim 1 wherein said pyridine is pyridine, said alkanol is methanol and said cobalt compound is cobalt carbonate.

13. The cobalt complex prepared by the process of claim 1 wherein said pyridine is pyridine, said alkanol is methanol, said cobalt compound is cobalt carbonate and said pyridine:methanol volume ratio is about 1:1.

14. A process for preparing solutions in pyridine/methanol of cobalt complexes which consists essentially of reacting (1) cobalt compound selected from cobalt oxides, cobalt sulfides, cobalt cyanides, cobalt salts of $H_2SO_4$, $H_2SO_3$, $HNO_3$, halogen acids, phosphorus acids, boric acids and carbonic acids, organic cobalt salts of sulfonic acids, phosphorus containing acids, and $C_2$–$C_{20}$ carboxylic acids, (2) carbon monoxide, (3) hydrogen, (4) a pyridine selected from isoquinoline, pyridine and mono- and di-alkyl substituted pyridines wherein the alkyls are $C_1$–$C_6$, and (5) $C_1$–$C_{10}$ alkanol such that (i) the molar ratio of $H_2$:CO is from 1:10 to 10:1, (ii) the molar ratio of said pyridine:cobalt is greater than about 2:1, and (iii) the volume ratio of pyridine:alkanol is from 3:1 to 1:3, at pressures ranging from about 1,000 to about 10,000 p.s.i.g., and temperatures ranging from 100°C. to 250°C.

15. The process of claim 14 wherein said $H_2$:CO molar ratio is 1.5:1 to 1:3 and said pyridine:alkanol volume ratio is about 1:1.

16. The process of claim 14 wherein said pyridine is pyridine.

17. The process of claim 14 wherein said alkanol is methanol.

18. The process of claim 17 wherein said cobalt compound is a cobalt salt of a $C_2$–$C_{20}$ carboxylic acid and said pyridine is pyridine.

19. The process of claim 17 wherein said alkanol is methanol.

20. The process of claim 19 wherein said cobalt compound is cobalt carbonate.

21. The process of claim 20 wherein said $H_2$:CO ratio is 1:1 to 1:3.

22. The process of claim 21 wherein said pyridine:methanol volume ratio is about 1:1.

23. The process of claim 22 wherein said $H_2$:CO ratio is about 1:2.

24. The solutions in pyridine/methanol of cobalt complex prepared by the process of claim 14 wherein said cobalt compound is a cobalt salt of a $C_2$–$C_{20}$ carboxylic acid, said alkanol is methanol and said pyridine is pyridine.

25. The solutions in pyridine/methanol of cobalt complex prepared by the process of claim 14 wherein said pyridine is pyridine, said alkanol is methanol and said cobalt compound is cobalt carbonate.

26. The solutions in pyridine/methanol of cobalt complex prepared by the process of claim 14 wherein said pyridine is pyridine, said alkanol is methanol, said cobalt compound is cobalt carbonate and said pyridine:methanol volume ratio is about 1:1.

* * * * *

UNITED STATES PATENT AND TRADEMARK OFFICE
CERTIFICATE OF CORRECTION

PATENT NO. : 3,935,228
DATED : January 27, 1976
INVENTOR(S) : Kestutis A. Keblys It is certified that error appears in the above-identified patent and that said Letters Patent are hereby corrected as shown below:

Column 2, lines 33-34, "4-ethyl-3,3-dimethylpyridine," should be -- 4-ethyl-3,5-dimethylpyridine, --

Column 5, line 32 -- is -- (second instance) should be deleted

Column 5, lines 39-40, "consideration" should be -- operation --

Signed and Sealed this eighteenth Day of May 1976

[SEAL]

Attest:

RUTH C. MASON
*Attesting Officer*

C. MARSHALL DANN
*Commissioner of Patents and Trademarks*